United States Patent [19]

Maryanoff et al.

[11] Patent Number: 5,968,946
[45] Date of Patent: Oct. 19, 1999

[54] HETEROCYCLIC DERIVATIVES USEFUL IN TREATING CENTRAL NERVOUS SYSTEM DISORDERS

[75] Inventors: Bruce E. Maryanoff, Forest Grove; David McComsey, Warminster; James J. McNally, Souderton; Samuel O. Nortey, LaMott; Allen B. Reitz, Lansdale, all of Pa.

[73] Assignee: Ortho-McNeil Pharmaceutical, Inc., Raritaon, N.J.

[21] Appl. No.: 09/166,327

[22] Filed: Oct. 5, 1998

Related U.S. Application Data

[60] Provisional application No. 60/061,248, Oct. 7, 1997.

[51] Int. Cl.$^6$ .................. A61K 31/44; C07D 471/14
[52] U.S. Cl. .................................. 514/293; 546/82
[58] Field of Search ................... 546/82; 514/293

[56] References Cited

U.S. PATENT DOCUMENTS 5,639,760  6/1997  Maryanoff ........................ 514/292
5,817,668  10/1998  Reitz ............................... 514/292

*Primary Examiner*—Evelyn Mei Huang
*Attorney, Agent, or Firm*—Ralph R. Palo

[57] ABSTRACT

This invention relates to a series of substituted 3-oxo-pyrrolo[1,2-a]imidazopyridine derivatives of the formula 1

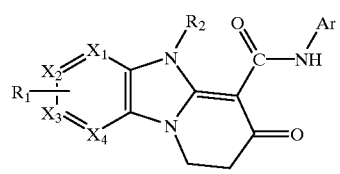

where $X_1$–$X_4$, $R_1$, $R_2$ and Ar are defined herein. In addition the invention relates to pharmaceutical compositions containing them and intermediates used in their manufacture. The compounds of the invention are ligands for the benzodiazepine site on the GABA-A receptor and display anxiolytic and anticonvulsant activity in animal models.

15 Claims, No Drawings

HETEROCYCLIC DERIVATIVES USEFUL IN TREATING CENTRAL NERVOUS SYSTEM DISORDERS

This application claims the benefit of provisional application No. 60/061,248, filed Oct. 7, 1997.

This invention relates to a series of substituted oxo-dipyridoimidazole derivatives, pharmaceutical compositions containing them and intermediates used in their manufacture. The compounds of the invention are ligands for the benzodiazepine site on the GABA-A receptor and display anxiolytic and anticonvulsant activity in animal models.

BACKGROUND OF THE INVENTION

The gamma-aminobutyric acid-A receptor (GABA-A receptor) is the most abundant inhibitory receptor in mammalian brain. It is comprised of a heteropolymeric structure that forms a chloride ion channel, and contains multiple recognition sites for the binding of molecules. The binding of GABA to its specific recognition site on the GABA-A receptor opens the ion channel and allows chloride ions to flow into the nerve cell. This action hyperpolarizes the cell membrane of that neuron and thereby makes the cell less reactive to excitatory stimuli. The chloride ion current may also be regulated by various drugs that serve as positive or negative modulators of the GABA-A receptor (Puia, G. et al. *Molecular Pharm.* 1991, 39, 691). The so-called benzodiazepine (BZD) receptor is a site for such allosteric modulators on the GABA-A receptor. This site mediates two opposing effects, one that amplifies the action of GABA ("positive" efficacy) and the other that reduces the action of GABA ("negative" efficacy). Agents facilitating GABA-receptor/chloride ion-channel functions via the BZD site are referred to as agonists, while agents reducing such function are referred to as inverse agonists. Antagonists at this site block the effects of agonists or inverse agonists by competitively inhibiting their binding. It is thus possible to have a series of compounds in which members equally bind to the BZD site but have equal and opposite regulatory effects on the GABA-A receptor/chloride ion channel. Also, within the series a continuum of activity is possible (Takada, S. et al. *J. Med. Chem.* 1988, 31, 1738). Thus, BZD receptor ligands can induce a wide spectrum of pharmacological effects ranging from muscle relaxant, hypnotic, sedative, anxiolytic, and anticonvulsant activities, produced by full or partial agonists ("positive"), to the proconvulsant, anti-inebriant, and anxiogenic activities, produced by inverse agonists ("negative"). (A further understanding of this area can be gleaned from: Mohler, H. *Arzneim.-Forsch./Drug Res.* 1992, 42 (2a), 211; Haefely, W. et al., *Advances in Drug Research*, Academic Press, vol. 14, 1985, pp. 165–322; Skolnick, P. et al., *GABA and Benzodiazepine Receptors*, Squires, R., Ed., 1987, pp. 99–102 and references cited therein.)

The benzodiazepines are a class of compounds which bind to the BZD receptor with high affinity. Most of the drugs in use are agonist-type ligands for the receptor. Such compounds are generally useful for their anticonvulsant, anxiolytic, sedative, and muscle relaxant effects. Antagonists of the BZD binding site are useful for the treatment of benzodiazepine drug overdose and inverse agonists are useful in managing alcoholism.

The present invention is concerned with novel compositions of matter based on oxo-dipyridoimidazole derivatives. Compounds having some structural similarity to those of the present invention are described in U.S. Pat. No. 5,639,760, Rida, S. M. et al. *J. Het. Chem.* 1988, 25, 1087; Soliman, F. S. G. et al. *Arch. Pharm.* 1984, 317, 951; Volovenko, Y. M. et al. U.S.S.R. Patent SU 1027166 (*Chem Abs.* 99(25) 212524t); Ohta, S. et al. *Heterocycles* 1991, 32, 1923; Ohta, S. et al. *Chem. Pharm. Bull.* 1991, 39, 2787.

SUMMARY OF THE INVENTION

The present invention is directed to compounds of Formula I

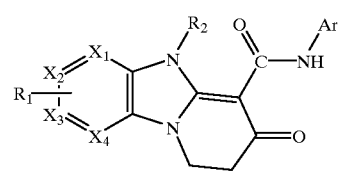

Ar is selected from the group consisting of $C_{1-12}$alkyl, cyclo $C_{3-10}$alkyl, phenyl; substituted phenyl (where the phenyl substituents are independently selected from one or more of halogen, $C_{1-5}$alkyl, perfluoro$C_{1-5}$alkyl, nitro, $C_{1-5}$alkoxy, amino, $C_{1-5}$alkylamino, di $C_{1-5}$alkylamino, cyano, carboxy, $C_{1-5}$alkoxycarbonyl, aminocarbonyl, and aminosulfonyl), ara$C_{1-5}$alkyl substituted ara$C_{1-5}$alkyl (where the phenyl substituents are independently selected from one or more of halogen, $C_{1-5}$alkyl, perfluoro$C_{1-5}$alkyl, nitro, $C_{1-5}$alkoxy, amino, $C_{1-5}$alkylamino, di$C_{1-5}$alkylamino, cyano, carboxy, $C_{1-5}$alkoxycarbonyl, aminocarbonyl, and aminosulfonyl), a heteroaryl containing 5 to 7 ring atoms where at least one ring atom is selected from nitrogen, oxygen or sulfur, a substituted heteroaryl containing 5 to 7 ring atoms where at least one ring atom is selected from nitrogen, oxygen or sulfur (where the substituents are independently selected from one or more of halogen, $C_{1-5}$alkyl and perfluoro$C_{1-5}$alkyl), heteroaryl$C_{1-2}$alkyl, and substituted heteroaryl$C_{1-2}$alkyl (where the substituents are independently selected from one or more of halogen, $C_{1-5}$alkyl and perfluoro$C_{1-5}$alkyl), $R_1$ is selected from the group consisting of hydrogen, $C_{1-12}$alkyl, $C_{1-5}$alkoxy, halogen, nitro, phenoxy, substitued phenoxy (where the phenyl substitutents are $C_{1-5}$alkyl and halogen), phenyl$C_{1-5}$alkoxy and substituted phenyl$C_{1-5}$alkoxy (where the phenyl substitutents are $C_{1-5}$alkyl and halogen);

$R_2$ is selected from the group consisting of hydrogen, $C_{1-12}$alkyl, $C_{3-10}$cycloalkyl, $C_{1-5}$alkoxy$C_{1-5}$alkyl, amino$C_{1-5}$alkyl, ara$C_{1-5}$alkyl, substituted ara$C_{1-5}$alkyl, (where the substituents are independently selected from one or more of halogen, $C_{1-5}$alkyl and perfluoro$C_{1-5}$alkyl) and heteroaryl$C_{1-5}$alkyl, where heteroaryl contains 5–7 ring atoms where at least one ring atom is selected from nitrogen, oxygen or sulfur;

$X_{1-X4}$ is N or C with the proviso that one and only one of $X_1$–$X_4$ is N and the rest are C; or pharmaceutically acceptable salts thereof.

The compounds of formula I are useful in treating central nervous system disorders. Particularly, the compounds are ligands for the BZD binding site on GABA-A receptors. Since the compounds are competitive binders for the BZD receptor, it is anticipated that they are useful as antidotes for benzodiazepine related drug overdoses, In addition, the compounds demonstrate anxiolytic, anticonvulsant, muscle relaxant and hypnotic/sedative activity in animal models. Aside from their demonstrated activity, the compounds are expected to be useful in a variety of CNS disorders related to the BZD binding site such as antiepileptics, anti-inebriants, and the like.

The present invention also comprises pharmaceutical compositions containing one or more of the compounds of formula I and methods for the treatment of disorders to the central nervous system including convulsions such as epileptic seizures, anxiety, muscular spasms, sleep disorders, and benzodiazepine overdoses employing a compound of formula I.

DETAILED DESCRIPTION OF THE INVENTION

As used herein unless otherwise noted the terms "alkyl" and "alkoxy" whether used alone or as part of a substituent group, include straight and branched chains. For example, alkyl radicals include methyl, ethyl, propyl, isopropyl, butyl, isobutyl, sec-butyl, t-butyl, pentyl, 2-methyl-3-butyl, 1-methylbutyl, 2-methylbutyl, neopentyl, hexyl, 1-methylpentyl, 3-methylpentyl. Alkoxy radicals are oxygen ethers formed from the previously described straight or branched chain alkyl groups.

The term "aryl" as used herein alone or in combination with other terms indicates aromatic hydrocarbon groups such as phenyl or naphthyl. The term "aralkyl" means a radical containing a lower alkyl group substituted with an aryl radical. With reference to substituents, the term "independently" means that when more than one of such substituent is possible, such substituents may be the same or different from each other.

The term "heteroaryl" includes aromatic compounds containing at least one heteroatom selected from nitrogen, oxygen, or sulfur. The heteroaryl compounds may consist of one or more aromatic rings fused together. Example of such heteroaryls include but are not restricted to the following: pyridine, pyridinylmethyl, thiazole, pyrimidine, indoline, quinoline, indazole, benzofuran, triazine, pyrazine, isoquinoline, isoxazole, thiazole, thiophene, thiadiazole, benzothiazole, triazole, and benzotriazole. The points of attachment of said heteroaryls is determined by the availability of known amino-substituted heteroaryls. For example, 2-aminopyridine, 3-aminopyridine, and 4aminopyridine are known and are used to prepare compounds the corresponding compounds of formula I.

When compounds contain a basic moiety, acid addition salts may be prepared and may be chosen from hydrochloric, hydrobromic, hydroiodic, perchloric, sulfuric, nitric, phosphoric, acetic, propionic, glycolic, lactic, pyruvic, oxalic, malonic, succinic, maleic, fumaric, malic, tartaric, citric, benzoic, cinnamic, mandelic, methanesulfonic, p-toluenesulfonic, cyclohexanesulfamic, salicylic, 2-phenoxybenzoic, 2-acetoxybenzoic, or saccharin, and the like. Such salts can are made by reacting the free base of compounds of formula I with the acid and isolating the salt.

Compounds of formula I can also be treated with a base to prepare the salt of the enolate formed. Such pharmaceutically acceptable salts may include but are not restricted to: alkali metal salts such as sodium or potassium; ammonium salts; monoalkylammonium salts; dialkylammonium salts; trialkylammonium salts; tetraalkylammonium salts; and tromethamine salts.

Hydrates and other solvates of the compound of formula I are also included within the scope of this invention and included within the definition of formula I.

The compounds of formula I may be prepared as outlined in Scheme 1.

An aminonitropyridine derivative II, such as 3-amino4-nitropyridine, may be treated with a mixture of acrylonitrile and a suitable base such as Triton B (N-benzyltriethylammonium hydroxide) in an appropriate solvent such as dioxane at room temperature for 1–4 days to give the illustrated nitrile derivative III. Treatment of derivative III with a suitable reduction catalyst such as Pd/C in an appropriate solvent such as ethyl acetate under hydrogen atmosphere of about 50–60 psig for about 3–12 h gives the amino derivative IV. This derivative may be heated with ethyl ethoxycarbonylacetimidate hydrochloride in a suitable solvent such as EtOH for about 4–24 h to give the the ester V. Treatment of derivative V with an anhydrous acid such as HCl(g) in an appropriate solvent such as EtOH at reflux for 4–24 h gives the diester VI. This diester may be treated with a suitable base such as sodium ethoxide in an appropriate solvent such as EtOH for about 12–24 h at room temperature followed by treatment with ethanolic HCl to give the derivative Derivative VII is heated to reflux with the appropriate substituted amine derivative VIII, such as 3-amino-1,2,4-triazole, in a suitable solvent such as xylene for about 1–24 h to give compounds of formula I, the amide derivatives IX. These compounds may be selectively alkylated in the N5 position using the method Mitsunobu (see Hughes, D. *Organic Reactions,* 42, 355–656) or the recently reported modified procedures (see Tsunoda, *Tetrahedron Letters* 1993, 34, 1639–1642 and Tsunoda, *Chemistry Letters* 1994, 539–542). Treatment of compounds IX with an appropriately substituted alcohol such as benzylalcohol and 1–5 equivalents of a suitable activating agent such as diethylazodicarboxylate (DEAD), azodicarbonyldipiperidine (ADDP), or 1,1-azobis(N,Ndimethylformamide) (TMAD) and an appropriate trisubstituted phosphine such as triphenylphosphine or tributylphosphine in an appropriate solvent such as benzene, THF, or DMF at about 0 degress C. to room temperature for about 1–24 hr can provide the desired N5-substituted pyrrolobenzimidazopyridine derivatives X.

This scheme may be used to produce all of the compounds of formula I. Although the illustrated scheme produces a compound where $X_1$, $X_2$, and $X_4$ are C, where $X_3$ is nitrogen, $R_1$ is hydrogen, $R_2$ is H (or aralkyl) and Ar is 1,2,4-triazol-3-yl, the starting material II may be modified to produce other substitution patterns. For example if one replaces the illustrated derivative II (3-amino4-nitropyridine) with 1-amino-2-nitropyridine and carries out the remaining steps as illustrated a compound of formula 1 where $X_2$, $X_3$, and $X_1$ are C, where $X_4$ is nitrogen, $R_1$ is hydrogen, $R_2$ is H (or aralkyl) and Ar is 1,2,4-triazol-3-yl is produced. To produce compounds where $R_1$ is other than hydrogen lf compounds are desired starting material II may be modified to one of the known substituted aminonitropyridines. For example, to produce a compound where $X_2$, $X_3$, and $X_1$ are C, where $X_4$ is nitrogen, $R_2$ is H (or aralkyl), Ar is 1,2,4-triazol-3-yl and there are 2 $R_1$s (3-chloro and 4-methyl), simply replace the illustrated starting material with 2-amino6-chloro-5-methyl-3-nitropyridine.

To produce compounds where Ar is other than 1,2,4-triazol-3-yl, replace the illustrated derivative VII with other amines such as 2,3 or 5-aminopyridine, 2-aminothiazole, 2-aminothiazole, aniline and the like. Finally to produce compounds where $R_2$ is other than benzyl, replace, the alkylating agent with an alkanol such as ethanol.

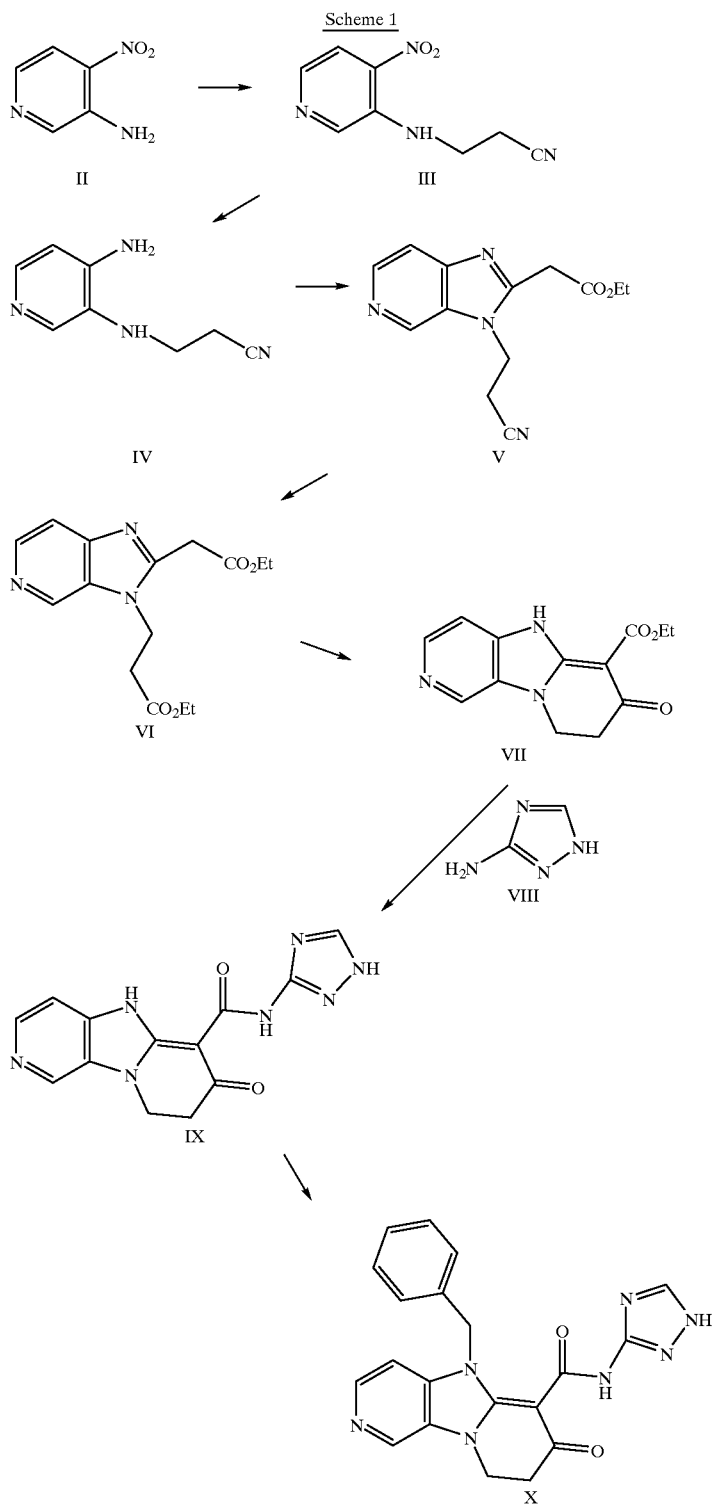

Scheme 1

The compounds of this invention were tested for affinity for the benzodiazepine sites of the GABA-A receptor. Since compounds which bind to this receptor can be useful in treating central nervous system disorders, the compounds were also tested in appropriate screens to evaluate specific activities. The results of the various screens are shown in Table 1. Not all compounds were tested in each of the screens. A blank next to a particular compound indicates that the compound was not tested in that screen.

Benzodiazepine Receptor Binding Assay

Selected compounds, which were prepared according to the experimental details given in the following examples, were tested for binding to the benzodiazepine site of the GABA-A receptor (Williams, M. et al., *J. Pharm. Exper. Therap.* 1988, 248, 89). The ability of the compounds of the invention to inhibit the binding of flunitrazepam to prepared receptors was assessed. For each sample, membranes from ca. 10 mg of tissue were incubated in a $K_2HPO_4$-buffered incubation medium (final concentration=2.0 mL). The concentration of ligand ($^3$H-flunitrazepam) was ca. 3 nM. Samples were incubated 10–20 min at 25° C., after which the membrane material and bound ligand was collected on glass fiber filter sheets using vacuum filtration. The collected material was washed with 10 mM HEPES buffered solution, and the radioactivity associated with each sample was measured by liquid scintillation spectrometry. The binding of the test drug to the receptor was determined by comparing the amount of radiolabeled ligand bound in control samples to the amount of ligand bound in the presence of the drug. Concentration-response data were analyzed in a variety of ways. The $IC_{50}$ was usually calculated by transforming the data to a log-logit format, then performing a linear regression analysis. This procedure provides a Hill coefficient as well as the $IC_{50}$ value. The $IC_{50}$ (value, for all tested compounds is listed in Tables 1. An $IC_{50}$ value of over 10,000 for a particular compound indicates that the compound was not active in this screen. This screen is a general screen and compounds active in this screen are considered active in treating one or more disorders of the central nervous system.

Assay to Measure the Suppression of Anxiety in the Adult Male Rat

The anxiolytic activity of selected compounds of the invention was assessed by determining their ability to encourage behavior that had been suppressed by punishment (Vogel, J. R. et al. *Psychopharmacology* 1971, 21, 1). Male rats were deprived of water for 48 hours and were deprived of food for 24 hours prior to testing. After the first 24 hours of water deprivation, they were placed in the conflict chamber for a training period; wherein, they were allowed 200 unpunished licks from a bottle containing tap water. The experiment was run the next day. At the expected time of peak activity, the animals were placed in the chamber and allowed access to tap water. If they failed to drink, the experiment was terminated in 5 min, and animals were evaluated for signs of CNS depression. Their first lick initiates a 3-min test session. Subsequently, every 20th lick was punished by a 0.2-s shock delivered via the stainless-steel drinking-tube. Vehicle-treated control animals generally were willing to accept a median number of 3 to 8 shocks per test session. Animals treated with an active anxiolytic drug tolerated significantly more shocks than control animals. The Wilcoxon rank-sum test (Mann-Whitney U-test) was used to test for an increase (p<0.05, 1-tailed) in the median number of shocks in drug-treated groups, compared to a concurrently run vehicle-treated group. The biological assay is considered to be valid if the effects of a known anxiolytic (positive control) are detected, within the same experiment. A compound was considered active if there is a significant difference in the median number of shocks tolerated between the drug-treated group and the control group. The minimum effective doses (MED) for the active compounds of the invention are listed in Tables 1. The MED was defined as the minimum dose of the drug-treatment as analyzed using the Wilcoxon rank-sum test (SAS; Statistical Analysis System, version 5.16). If the MED value is greater than 10, an active dose of the compound being tested had not been determined.

Assay to Determine the Suppression of Metrazol-Induced Convulsions in Adult Male Rats and Mice Selected compounds of the invention were tested for their ability to reduce metrazol-induced convulsions in mice (Swinyard, E. A. *J. Am. Pharm Assoc.* 1949, 38, 201). Male $CD_1$ mice, were fasted at least 16 hours, were divided into equal groups and test compounds or vehicle were administered parenterally. Water was not withheld except during the period of observations. At the time of suspected peak activity, anti-pentylenetetrazol (anti-metrazol) activity was evaluated by the subcutaneous administration of the $CD_{90}$ dose of metrazol (the dose of metrazol was determined from the dose-response curve producing clonic convulsions in 90% of animals that received the corresponding vehicle for this experiment). Metrazol was dissolved in 0.9% sodium chloride solution, and its dose volume was 10 ml/kg. Animals were housed individually for observation of clonic convulsions, tonic convulsions and death for a period of 30 min. Test compounds that blocked the clonic seizure component of the convulsion in at least 50% of the animals were considered active. The biological assay was considered to be valid if the effects of a known anticonvulsant (positive control) were detected, within the same experiment. Activity was reported as percent reduction of clonic convulsions from the vehicle group. The $ED_{50}$ values of active compounds were calculated by the method of probits (Finney, D. J. 1971. Probit Analysis. London: Cambridge University Press) and are listed in Tables 1. An $ED_{50}$ value of greater than 30 indicates that an active dose for the compound being tested had not been determined. Compounds active in this screen are considered active anticonvulsant/antiepileptic agents.

Horizontal Screen Test for Motor Coordination

Some of the compounds of the invention were tested for their ability to act as general CNS agents and particularly as skeletal muscle relaxants and hypnotics/sedatives (Coughenour, L. L. et al. *Pharm. Biochem. Behav.* 1977, 6, 351). Male $CD_1$ mice, fasted for at least 16 hours but allowed access to water except during the period of observation, were placed on a horizontally-held screen (mesh size ¼", wire diameter approximately 1.0 mm). The screen was inverted and mice which successfully climb to the top side of the screen within one minute were selected for testing. Selected mice were weighed and divided into equal groups. Test compounds or vehicle were administered to those mice parenterally. At a pre-determined interval (or intervals) after administration, the animals were tested for their ability to climb to the top side of the inverted screen (pass the test). Activity is reported as the percent reduction in the number of animals that pass the test in each treatment group relative to the corresponding vehicle-treated group. Percent Reduction=100×([Percent Pass in Vehicle Group]−[Percent Pass in Test Group]/Percent Pass in Vehicle Group). Test compounds which produce a 50% or greater reduction in the number passing the test were considered active. $ED_{50}$ values of the active compounds were calculated by the method of probits (Finney, D. J. 1971. Probit Analysis. London: Cambridge University Press) and are listed in Tables 1 to 5. An $ED_{50}$ value of greater than 300 indicates that an active dose for the compound being tested had not been determined.

TABLE 1

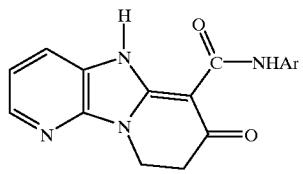

| CP # | Ar | Anticonflict MED (mg/kg) PO | IP | Antimetrazol ED$_{50}$ (mg/kg) PO | IP | Horizontal screen ED$_{50}$ (mg/kg) PO | IP | $^3$H-Flunitrazepam IC50 |
|---|---|---|---|---|---|---|---|---|
| 1 | 2-FPh | >30 | >10 | >30 | 10 | >30 | 10 | 291 |
| 2 | Ph | >30 | >10 | >30 | >10 | >30 | >10 | >4348 |
| 3 | 4-pyridyl | >30 | >10 | >30 | >10 | >30 | >10 | >10000 |
| 4 | 2,4,6-F$_3$Ph | >30 | >10 | >30 | ca 10 | >30 | ca 10 | 1960 |

TABLE 2

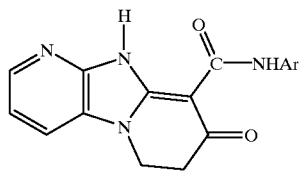

| CP # | Ar | Anticonflict MED (mg/kg) PO | IP | Antimetrazol ED$_{50}$ (mg/kg) PO | IP | Horizontal screen ED$_{50}$ (mg/kg) PO | IP | $^3$H-Flunitrazepam IC50 |
|---|---|---|---|---|---|---|---|---|
| 5 | 2-FPh | >30 | 10 | 10 | 1 | >30 | 3 | 3.5 |
| 6 | Ph | 30 | >10 | <30 | 3 | >30 | 3 | 8.3 |
| 7 | 4-pyridyl | 10 | 30 | >10 | >30 | >10 | | 619 |
| 8 | 2,4,6-F$_3$Ph | >30 | >10 | >30 | 10 | >30 | >30 | 220 |
| 9 | 2,6-F$_2$Ph | >10 | >10 | ca. 30 | ca. 30 | >30 | ca. 10 | 30.1 |

TABLE 3

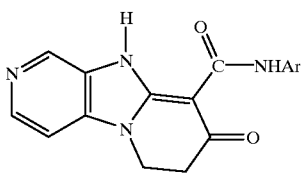

| CP # | Ar | Anticonflict MED (mg/kg) PO | IP | Antimetrazol ED$_{50}$ (mg/kg) PO | IP | Horizontal screen ED$_{50}$ (mg/kg) PO | IP | $^3$H-Flunitrazepam IC50 |
|---|---|---|---|---|---|---|---|---|
| 10 | 2,6-F$_2$Ph | ca. 3 | >10 | >30 | >10 | — | | 17.7 |

TABLE 4

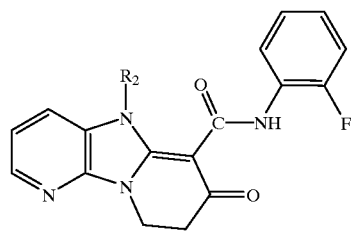

| | | Anticonflict MED (mg/kg) | | Antimetrazol ED$_{50}$ (mg/kg) | | Horizontal screen ED$_{50}$ (mg/kg) | | $^3$H-Flunitrazepam |
|---|---|---|---|---|---|---|---|---|
| CP # | R$_2$ | PO | IP | PO | IP | PO | IP | IC50 |
| 11 | MeO(CH$_2$)$_2$ | >10 | | | | | | 285 |
| 12 | CH$_3$ | >10 | | | | | | >312 |

Although the claimed compounds are useful as modulators of the benzodiazepine receptor, some compounds are more active than others. These compounds are either preferred or particularly preferred.

Examples of preferred compounds include:

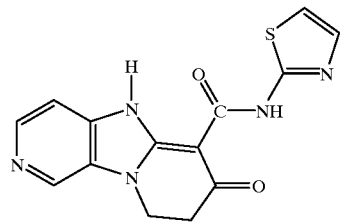

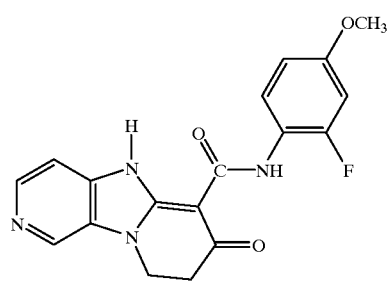

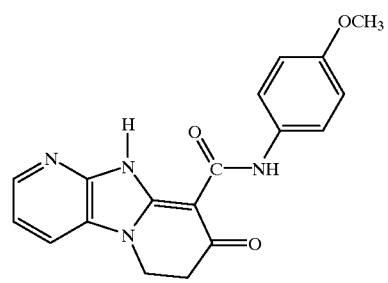

-continued

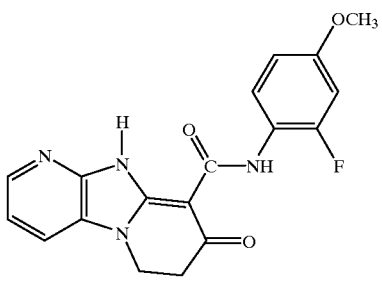

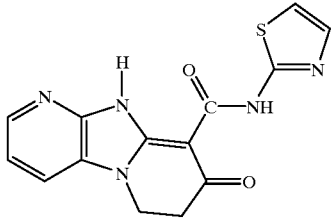

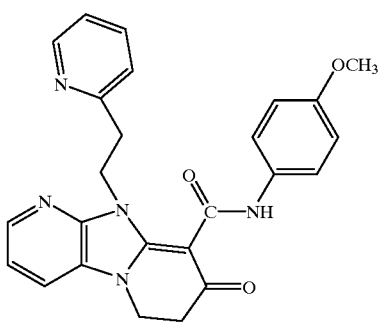

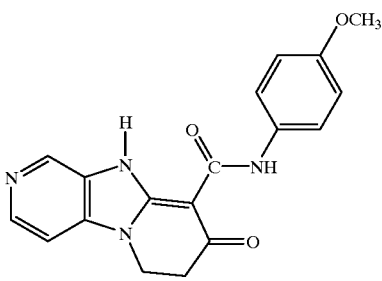

and

-continued

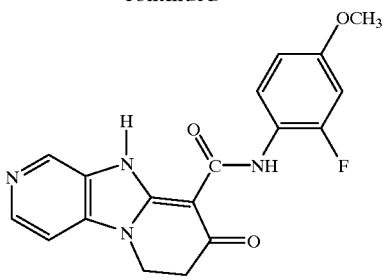

Examples of particularly preferred compounds of formula I include:

8,9-dihydro-7-keto-N-(2-fluorophenyl)dipyrido [1,2-a:3',2'-d]imidazole-6-carboxamide-5-methoxyethyl; i.e., where $R_1$ is hydrogen, $R_2$ is methoxyethyl, $X_4$ is nitrogen, $X_1=X_2=X_3=CH$, Ar is 2-fluorophenyl;

6,7-dihydro-8-keto-N-(2-fluorophenyl)dipyrido[1,2-a:2',3'-d]imidazole-9-carboxamide; i.e., where $R_1$ and $R_2$ is hydrogen, $X_1$ is nitrogen, $X_2=X_3=X_4=CH$, Ar is 2-fluorophenyl;

6,7-dihydro-8-keto-N-phenyldipyrido[1,2-a:2',3'-d]imidazole-9-carboxamide; i.e., where $R_1$ and $R_2$ is hydrogen, $X_1$ is nitrogen, $X_2=X_3=X_4=CH$, Ar is phenyl;

6,7-dihydro-8-keto-N-(4-pyridyl)dipyrido[1,2-a:2',3'-d]imidazole-9-carboxamide; i.e., where $R_1$ and $R_2$ is hydrogen, $X_1$ is nitrogen, $X_2=X_3=X_4=CH$, Ar is 4-pyridyl;

6,7-dihydro-8-keto-N-(2,4,6-trifluorophenyl)dipyrido[1,2-a:2',3'-d]imidazole-9-carboxamide; i.e., where $R_1$ and $R_2$ is hydrogen, $X_1$ is nitrogen, $X_2=X_3=X_4=CH$, Ar is 2,4,6-trifluorophenyl;

6,7-dihydro-8-keto-N-(2,6-difluorophenyl)dipyrido[1,2-a:2',3'-d]imidazole-9-carboxamide; i.e., where $R_1$ and $R_2$ is hydrogen, $X_1$ is nitrogen, $X_2=X_3=X_4=CH$, Ar is 2,6-difluorophenyl; and 6,7-dihydro-8-keto-N-(2,6-difluorophenyl)dipyrido[1,2-a:3',4'-d]imidazole-9-carboxamide; i.e., where $R_1$ and $R_2$ is hydrogen, $X_2$ is nitrogen, $X_1=X_3=X_4=CH$, Ar is 2,6-difluorophenyl.

To prepare the pharmaceutical compositions of this invention, one or more compounds or salts thereof, as the active ingredient, is intimately admixed with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will preferably contain per dosage unit, e.g., tablet, capsule, powder, injection, teaspoonful and the like, from about 5 to about 500 mg of the active ingredient, although other unit dosages may be employed.

In therapeutic use in treating disorders of the central nervous system in mammals, the compounds of this invention may be administered in an amount of from about 0.2 to 25 mg/kg per day. In therapeutic use as an anxiolytic, the compounds of the invention may be administered in an amount from about 0.2 to 25 mg/kg per day. In therapeutic use as an anticonvulsant/antiepileptic, the compounds of the invention may be administered in an amount from about 0.2 to 25 mg/kg per day. In therapeutic use as an agent for treating benzodiazepine overdoses, the compounds of the invention may be administered in an amount from about 0.2 to 25 mg/kg per day. In therapeutic use as a sedative/hypnotic, a therapeutically effective amount is from about 0.2 to 25 mg/kg per day. As a muscle relaxant about 0.2 to 25 mg/kg per day of the compounds of this invention may be used. Determination of optimum dosages for a particular situation is within the capabilities of formulators.

In order to illustrate the invention, the following examples are included. These examples do not limit the invention. They are meant to illustrate and suggest a method of practicing the invention. Although there are other methods of practicing this invention, those methods are deemed to be within the scope of this invention.

EXAMPLES

Melting point determinations were carried out on a Thomas Hoover or Mel-Temp melting point apparatus and are corrected unless otherwise specified. Each compound has at least two analytical results (elemental analysis, IR, $^1H$ NMR, MS) that are consistent with its assigned structures. The infrared spectra (KBr) were recorded on a Nicolet SX 60 FT spectrometer and are expressed in reciprocal centimeters. Nuclear magnetic resonance (NMR) spectra for hydrogen atoms were measured in the indicated solvent with tetramethylsilane (TMS) as the internal standard on a Bruker AM-360 (360 MHz), AM-400 (400 MHz), or AT-300 (300 MHz) spectrometer. The values are expressed in parts per million downfield from TMS. The elemental analyses were measured by Atlantic Microlabs (Atlanta, Ga.), Galbraith Labs (Knoxville, Tenn.) or in house and are expressed in percentage by weight of each element per total molecular weight. The mass spectra (MS) were determined on a Finnigan 3300 spectrometer (methane), using desorption chemical ionization techniques. All preparative column chromatography were run using a Waters Prep 500A HPLC (silica gel) employing the appropriate commercially available solvent. Unless otherwise noted, the materials used in the examples were obtained from readily available commercial suppliers or synthesized by standard methods known to anyone skilled in the art of chemical synthesis. The substituent groups, which vary between examples are hydrogen unless otherwise noted.

Example 1

8,9-Dihydro-7-keto-N-phenyldipyrido [1,2-a:3',2'-d]imidazole-6-carboxamide (CP #2)

A 40% solution of benzyltrimethylammonium hydroxide in MeOH (3.4 mL) was added to a solution of 2-amino-3- nitropyridine (50 g, 0.34 moles) in dioxane (800 mL) at room temperature. Acrylonitrile (84.4 mL, 1.28 moles) was added dropwise to the reaction mixture which was maintained at a temperature of 35–40° C. by means of an external ice bath. The resulting mixture was stirred at room temperature for 24 h and concentrated under vacuum to give a dark yellow solid (73.0 g), which was recrystallized three times in 95% ethanol to give the appropriate nitrile derivative III (29.7 g, 45% yield) as a light yellow solid.

A solution of this nitrile derivative III (29.2 g, 0.15 mol) and 10% Pd/C (3.0 g) in THF (750 mL) was placed in a Parr bottle and pressurized at 50–60 psig for 3–4 h. The resulting was filtered and concentrated in vacuo to give the desired amino nitrile derivative IV as a semisolid.

A mixture of this aminonitrile derivative IV (25.23 g, 0.16 mol), ethylethoxycarbonylacetimidate hydrochloride (61.4 g, 0.32 mole) in absolute EtOH (390 mL) was heated under reflux under argon for 12 h and was allowed to cool to room temperature overnight. The mixture was filtered, and filtrate concentrated in vacuo to a gray residue, which was redissolved in methylene chloride, washed once with water, once with brine, dried ($Na_2SO_4$), filtered, and concentrated in vacuo. The residue was recrystallized in IPA to give the appropriate cyanoalkyl pyridoimidazole V as a pale yellow solid.

Cyanoalkyl pyridoimidazole derivative V (23 g, 0.09 mol) was treated with 6N ethanolic HCL (470 mL) and the mixture was stirred under argon for 14 h. The solution was concentrated in vacuo to a syrup, which was treated with ice and water, neutralized with 15% NaOH (temperature of solution kept below 40° C.) to pH 8 and extracted into ethyl acetate, washed with brine, dried ($Na_2SO_4$) filtered, and concentrated in vacuo to give desired diester VI as a light brown syrup.

Sodium (2.02 g, 0.09 mol) was added to a stirred solution of absolute EtOH (250 mL) under argon atmosphere until all solids dissolved. A solution of diester derivative VI (25 g, 0.08 mol) was added dropwise to this solution, and the mixture was stirred for 24 h. The mixture was concentrated in vacuo to a yellow solid, which was suspended in water (50 mL) and the pH was adjusted to 8 with 1N HCL. The resulting solid was isolated (filtered) and air dried to give the appropriate pyrroloimidazopyrindine carboxylate VII as a solid: mp 234–237.

Anal. Calcd for $C_{13}H_{13}N_3O_3$ C, 60.22; H, 5.05; N, 16.21
Found: C, 60.00; H, 5.00; N, 15.76

The derivative VII ($X_1=X_2=X_3=H$, $X_4=N$, 1.5 g, 5.8 mmol) and aniline (1.22 g, 13.2 mmol) were combined in xylenes (60 mL) and heated to reflux for 6 h in a flask fitted with a Dean Stark trap. The resulting solid was filtered from the cooled reaction mixture and recrystallized from a mixture of methylene chloride and methanol to give compound #2 as a light yellow solid: mp 240–244° C.; Cl-ms: m/z 307 (M+1).

Anal. Calcd for $C_{17}H_{14}N_4O_2$: C, 66.66; H, 4.61; N, 18.29
Found: C, 66.56; H, 4.66; N, 18.29

Compounds #1, 3, and 4 were prepared in the same manner, and their physical properties are listed in Table 4.

Example 2 C P.s #5–9

3-Amino-2-nitropyridine was synthesized by the method decribed in U.S. Pat. No. 4,952,697; by reacting 3-aminopyridine with urea, nitrating the product formed to di(nitropyridyl)urea followed by hydrolysis.

An appropriately substituted aminonitropyridine was converted to a substituted derivative VII ($X_2=X_3=X_4=H$, $X_1=N$; 1 mmolar equivalent) by the method used in Example 1. This dipyridoimidazole carboxylate was then combined with a suitable amine (1.2–3.0 mmolar equivalents) in xylenes (5 mL) and heated at reflux for 1–6 h in a flask which may sometimes be fitted with a Dean Stark trap. The resulting solid was isolated from the reaction mixture and recrystallized from a suitable solvent to give the desired dipyridoimidazole carboxamide derivative VIII (compounds #5–9) as a solid.

TABLE 5

| CP # | Ar | m.p. ° C. | C | H | N | Empirical Formula |
|---|---|---|---|---|---|---|
| 1 | 2-FPh | 263–265 | 62.86 | 3.92 | 17.33 | $C_{17}H_{13}FN_4O_2$ |
| 2 | Ph | 240–244 | 66.58 | 4.66 | 18.29 | $C_{17}H_{14}N_4O_2$ |
| 3 | 4-pyridyl | 268–269 | 61.52 | 4.22 | 22.56 | $C_{16}H_{13}N_4O_2$[a] |
| 4 | 2,4,6-$F_3$Ph | 214–216 | 56.92 | 3.49 | 15.29 | $C_{17}H_{11}F_3N_4O_2$[b] |

Solvates present (moles): [a]0.20 $H_2O$; [b]0.25 ethanolate

TABLE 6

| CP # | Ar | m.p. ° C. | C | H | N | Empirical Formula |
|---|---|---|---|---|---|---|
| 5 | 2-FPh | 271–274 | 62.64 | 3.84 | 17.31 | $C_{17}H_{13}FN_4O_2$ |
| 6 | Ph | 259–261 | 66.37 | 4.32 | 18.47 | $C_{17}H_{14}N_4O_2$ |
| 7 | 4-pyridyl | 305–307 | 62.07 | 4.03 | 22.49 | $C_{16}H_{13}N_5O_2$[c] |
| 8 | 2,4,6-$F_3$Ph | 283–284 | 58.16 | 2.93 | 15.49 | $C_{17}H_{11}F_3N_4O_2$ |
| 9 | 2,6-$F_2$Ph | 271–273 | 59.61 | 3.53 | 16.39 | $C_{17}H_{12}F_2N_4O_2$ |

Solvates present (moles): [c]0.10 $H_2O$.

TABLE 7

| CP # | Ar | m.p. ° C. | C | H | N | Empirical Formula |
|---|---|---|---|---|---|---|
| 10 | 2,6-$F_2$Ph | 205–207 | 50.88 | 3.86 | 13.81 | $C_{17}H_{12}F_2N_4O_2$[d] |

Solvates present (moles): [d]1.2 $H_2O$. Purified as the mono hydrochloric acid salt.

Example 3

6,7-Dihydro-8-keto-N-(2,6-Difluorophenyl)dipyrido [1,2-a:3',4'-d]imidazole-9-carboxamide, CP #10

4-Amino-3-nitropyridine was synthesized by a literature reference [Harris M. G. and Stewart R. *Can. J. Chem.* 55, 3800 (1977)]; by nitration of 4-aminopyridine with conc. sulfuric acid and fuming nitric acid. This aminonitropyridine was then converted to the aminopropionitrile derivative IV by the method described in Example 1.

A mixture of aminopropionitrile derivative IV ($X_1$=$X_3$=$X_4$=H, $X_2$=N, 110.03 g, 0.062 mol), triethylamine (6.90 g, 0.068 mol) in methylene chloride (300 mL) was cooled to 5° C. and treated with ethyl malonyl chloride (10.25 g, 0.068 mole). The reaction mixture was stirred at room temperature for 18 h. The mixture was filtered, and filtrate was concentrated in vacuo to a gray residue, which was heated neat at 142° C. for 30 min, cooled and purified on prep 500 HPLC (eluted: EtOAc/MeOH: 16:1) to give the appropriate cyanoalkyl pyridoimidazole V as a light yellow solid.

The appropriate cyanoalkyl pyridoimidazole derivative V (1.52 g, 5.9 mmol) was treated with 6N ethanolic HCl (50 mL) and the mixture was stirred under argon for 5 h. The solution was concentrated in vacuo to a syrup, which was treated with ice and water, neutralized with 15% NaOH (temperature of solution kept below 40° C.) to pH 8 and extracted into ethyl acetate, dried ($Na_2SO_4$) and concentrated in vacuo to give desired diester VI as a light brown syrup.

Sodium (0.13 g, 0.006 mol) was added to a stirred solution of absolute EtOH (40 mL) under argon atmosphere untill all of the solids dissolved. A solution of the diester derivative VI (1.00 g, 3.3 mmol) in absolute ethanol (10 mL) was added dropwise to this solution, and mixture stirred for 6.5 h. Mixture was cooled to 5° C. and treated with 6N ethanolic hydrochloric acid to pH=7. The resultant solid was filtered to give derivative VII as a light yellow solid.

The carboxylate derivative VII (0.35 g, 1.4 mmol) and 2,6-difluoroaniline (0.23 g, 1.8 mmol) were combined in xylenes (10 mL) and heated to reflux for 6 h. The resulting solid was filtered from the cooled reaction mixture and treated with ethanolic HCl to give the crude hydrochloric acid salt which was recrystallized from 95% ethanol to give the title compound as a light yellow solid: mp 205–207° C.; Cl-ms: m/z 343 (M+1).

Anal. Calcd for $C_{17}H_{14}F_2N_4O_2 \cdot HCl \cdot 1.2H_2O$ C, 51.00; H, 3.87; N, 13.99

Found: C, 50.88; H, 3.86; N, 13.81

What is claimed is:

1. A compound of the formula I wherein:

Ar is selected from the group consisting of $C_{1-12}$alkyl, cyclo$C_{3-10}$alkyl, phenyl; substituted phenyl (where the phenyl substituents are independently selected from one or more of halogen, $C_{1-5}$alkyl, perfluoro$C_{1-5}$alkyl, nitro, $C_{1-5}$alkoxy, amino, $C_{1-5}$alkylamino, di $C_{1-5}$alkylamino, cyano, carboxy, $C_{1-5}$alkoxycarbonyl, aminocarbonyl, and aminosulfonyl), ara$C_{1-5}$ alkyl, substituted ara$C_{1-5}$alkyl (where the phenyl substituents are independently selected from one or more of halogen, $C_{1-5}$alkyl, perfluoro$C_{1-5}$alkyl, nitro, $C_{1-5}$alkoxy, amino, $C_{1-5}$alkylamino, di$C_{1-5}$alkylamino, cyano, carboxy, $C_{1-5}$alkoxycarbonyl, aminocarbonyl, and aminosulfonyl), a heteroaryl containing 5 to 7 ring atoms where at least one ring atom is selected from nitrogen, oxygen or sulfur, a substituted heteroaryl containing 5 to 7 ring atoms where at least one ring atom is selected from nitrogen, oxygen or sulfur (where the substituents are independently selected from one or more of halogen, $C_{1-5}$alkyl and perfluoro$C_{1-5}$alkyl), and heteroaryl$C_{1-2}$alkyl, substituted heteroaryl$C_{1-2}$ alkyl (where the substituents are independently selected from one or more of halogen, $C_{1-5}$alkyl and perfluoro$C_{1-5}$alkyl);

$R_1$ is selected from the group consisting of one or more of hydrogen, $C_{1-12}$alkyl, $C_{1-5}$alkoxy, halogen, nitro, phenoxy, substitued phenoxy (where the phenyl substitutents are $C_{1-5}$alkyl and halogen), phenyl$C_{1-5}$alkoxy and substituted phenyl$C_{1-5}$alkoxy (where the phenyl substitutents are $C_{1-5}$alkyl and halogen);

$R_2$ is selected from the group consisting of hydrogen, hydrogen, $C_{1-12}$alkyl, $C_{3-10}$cycloalkyl, $C_{1-5}$alkoxy$C_{1-5}$ alkyl, amino$C_{1-5}$alkyl, ara$C_{1-5}$alkyl, substituted ara$C_{1-5}$ alkyl, (where the substituents are independently selected from one or more of halogen, $C_{1-5}$alkyl and perfluoro$C_{1-5}$alkyl) and heteroaryl$C_{1-5}$alkyl, where heteroaryl contains 5–7 ring atoms where at least one ring atom is selected from nitrogen, oxygen or sulfur;

$X_1$–$X_4$ is N or C with the proviso that one and only one of $X_1$–$X_4$ is N and the rest are C;

or a pharmaceutically acceptable salt thereof.

2. The compound of claim 1 wherein:

Ar is $C_{1-12}$alkyl, cyclo$C_{3-10}$alkyl, phenyl; substituted phenyl, ara$C_{1-5}$alkyl or substituted ara$C_{1-5}$alkyl.

3. The compound of claim 1, wherein:

Ar is a heteroaryl having 5 ring atoms where one or more atoms is nitrogen, oxygen or sulfur.

4. The compound of claim 1, wherein:

$R_2$ is H, $C_{1-5}$alkyl or aralkyl.

5. The compounds of claim 1, wherein there is one $R_1$ substitutent.

6. The compound of claim 1, wherein:

$R_1$ is selected from any of hydrogen, $C_{1-12}$alkyl, $C_{1-5}$alkoxy, halogen , or perfluorolower$C_{1-5}$alkyl.

7. A compound selected from the group consisting of 8,9-Dihydro-7-keto-N-(2-fluorophenyl)dipyrido [1,2-a: 3',2'-d]imidazole-6-carboxamide-5-methoxyethyl;

6,7-Dihydro-8-keto-N-(2-fluorophenyl)dipyrido[1,2-a:2', 3'-d]imidazole-9-carboxamide.

6,7-Dihydro-8-keto-N-phenyldipyrido[1,2-a:2',3'-d] imidazole-9-carboxamide.

6,7-Dihydro-8-keto-N-(4-pyridyl)dipyrido[1,2-a:2',3'-d] imidazole-9-carboxamide.

6,7-Dihydro-8-keto-N-(2,4,6-trifluorophenyl)dipyrido[1, 2-a:2',3'-d]imidazole-9-carboxamide.

6,7-Dihydro-8-keto-N-(2,6-difluorophenyl)dipyrido[1,2-a:2',3'-d]imidazole-9-carboxamide.

6,7-Dihydro-8-keto-N-(2,6-difluorophenyl)dipyrido[1,2-a:3',4'-d]imidazole-9-carboxamide.

8. A pharmaceutical composition comprising a compound of formula I:

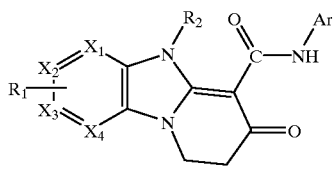

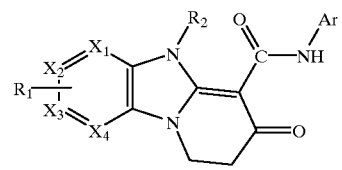

wherein:

Ar is selected from the group consisting of $C_{1-12}$alkyl, cyclo$C_{3-10}$alkyl, phenyl; substituted phenyl (where the phenyl substituents are independently selected from one or more of halogen, $C_{1-5}$alkyl, perfluoro$C_{1-5}$alkyl, nitro, $C_{1-5}$alkoxy, amino, $C_{1-5}$alkylamino, di$C_{1-5}$alkylamino, cyano, carboxy, $C_{1-5}$alkoxycarbonyl, aminocarbonyl, and aminosulfonyl), ara$C_{1-5}$alkyl, substituted ara$C_{1-5}$alkyl (where the phenyl substituents are independently selected from one or more of halogen, $C_{1-5}$alkyl, perfluoro$C_{1-5}$alkyl, nitro, $C_{1-5}$alkoxy, amino, $C_{1-5}$alkylamino, di$C_{1-5}$alkylamino, cyano, carboxy, $C_{1-5}$alkoxycarbonyl, aminocarbonyl, and aminosulfonyl), a heteroaryl containing 5 to 7 ring atoms where at least one ring atom is selected from nitrogen, oxygen or sulfur, a substituted heteroaryl containing 5 to 7 ring atoms where at least one ring atom is selected from nitrogen, oxygen or sulfur (where the substituents are independently selected from one or more of halogen, $C_{1-5}$alkyl and perfluoro$C_{1-5}$alkyl), heteroaryl$C_{1-2}$alkyl, and substituted heteroaryl$C_{1-2}$alkyl (where the substituents are independently selected from one or more of halogen, $C_{1-5}$alkyl and perfluoro$C_{1-5}$alkyl);

$R_1$ is selected from the group consisting of one or more of hydrogen, $C_{1-12}$alkyl, $C_{1-5}$alkoxy, halogen, nitro, phenoxy, substitued phenoxy (where the phenyl substitutents are $C_{1-5}$alkyl and halogen), phenyl$C_{1-5}$alkoxy and substituted phenyl$C_{1-5}$alkoxy (where the phenyl substitutents are $C_{1-5}$alkyl and halogen);

$R_2$ is selected from the group consisting of hydrogen, $C_{1-12}$alkyl, $C_{3-10}$cycloalkyl, $C_{1-5}$alkoxy$C_{1-5}$alkyl, amino$C_{1-5}$alkyl, ara$C_{1-5}$alkyl, substituted ara$C_{1-5}$alkyl, (where the substituents are independently selected from one or more of halogen, $C_{1-5}$alkyl and perfluoro$C_{1-5}$alkyl) and heteroaryl$C_{1-5}$alkyl, where heteroaryl contains 5–7 ring atoms where at least one ring atom is selected from nitrogen, oxygen or sulfur;

$X_1$–$X_4$ is N or C with the proviso that one and only one of $X_1$–$X_4$ is N and the rest are C;

or a pharmaceutically acceptable salt thereof in an amount effective for treating a disorder of the central nervous system selected from the group consisting of anxiety, convulsions, sleeplessness, muscle spasm, and benzodiazepine drug overdose and a pharmaceutically acceptable carrier or diluent.

9. A method for treating a disorder of the central nervous system selected from the group consisting of anxiety, convulsions, sleeplessness, muscle spasm, and benzodiazepine drug overdose consisting administering a compound of the formula I:

wherein:

Ar is selected from the group consisting of $C_{1-12}$alkyl, cyclo$C_{3-10}$alkyl, phenyl; substituted phenyl (where the phenyl substituents are independently selected from one or more of halogen, $C_{1-5}$alkyl, perfluoro$C_{1-5}$alkyl, nitro, $C_{1-5}$alkoxy, amino, $C_{1-5}$alkylamino, di$C_{1-5}$alkylamino, cyano, carboxy, $C_{1-5}$alkoxycarbonyl, aminocarbonyl, and aminosulfonyl), ara$C_{1-5}$alkyl and substituted ara$C_{1-5}$alkyl (where the phenyl substituents are independently selected from one or more of halogen, $C_{1-5}$alkyl, perfluoro$C_{1-5}$alkyl, nitro, $C_{1-5}$alkoxy, amino, $C_{1-5}$alkylamino, di$C_{1-5}$alkylamino, cyano, carboxy, $C_{1-5}$alkoxycarbonyl, aminocarbonyl, and aminosulfonyl), a heteroaryl containing 5 to 7 ring atoms where at least one ring atom is selected from nitrogen, oxygen or sulfur, a substituted heteroaryl containing 5 to 7 ring atoms where at least one ring atom is selected from nitrogen, oxygen or sulfur (where the substituents are independently selected from one or more of halogen, $C_{1-5}$alkyl and perfluoro$C_{1-5}$alkyl), heteroaryl$C_{1-2}$alkyl, substituted heteroaryl$C_{1-2}$alkyl (where the substituents are independently selected from one or more of halogen, $C_{1-5}$alkyl and perfluoro$C_{1-5}$alkyl);

$R_1$ is selected from the group consisting of one or more of hydrogen, $C_{1-12}$alkyl, $C_{1-5}$alkoxy, halogen, nitro, phenoxy, substitued phenoxy (where the phenyl substitutents are $C_{1-5}$alkyl and halogen), phenyl$C_{1-5}$alkoxy and substituted phenyl$C_{1-5}$alkoxy (where the phenyl substitutents are $C_{1-5}$alkyl and halogen);

$R_2$ is selected from the group consisting of hydrogen, $C_{1-2}$alkyl, $C_{3-10}$cycloalkyl, $C_{1-5}$alkoxy$C_{15}$alkyl, amino$C_{1-5}$alkyl, ara$C_{1-5}$alkyl, substituted ara$C_{1-5}$alkyl, (where the substituents are independently selected from one or more of halogen, $C_{1-5}$alkyl and perfluoro$C_{1-5}$alkyl) and heteroaryl$C_{1-5}$alkyl, where heteroaryl contains 5–7 ring atoms where at least one ring atom is selected from nitrogen, oxygen or sulfur;

$X_1$–$X_4$ is N or C with the proviso that one and only one of $X_1$–$X_4$ is N and the rest are C;

or a pharmaceutically acceptable salt thereof to a mammal affiliated with said disorder of the central nervous system in an amount effective for treating such disorder.

10. The method of claim 9, wherein the effective amount is of from about 0.2 to 25 mg/kg per day.

11. The method of claim 9, wherein the disorder is anxiety.

12. The method of claim 9 wherein the disorder is convulsions.

13. The method of claim 9 wherein the disorder is sleeplessness.

14. The method of claim 9 wherein the disorder is muscle spasm.

15. The method of claim 9 wherein the disorder is benzodiazepine drug overdose.

* * * * *

UNITED STATES PATENT AND TRADEMARK OFFICE
CERTIFICATE OF CORRECTION

PATENT NO. : 5,968,946
DATED : Oct. 19, 1999
INVENTOR(S) : Maryanoff et al.

It is certified that error appears in the above-identified patent and that said Letters Patent is hereby corrected as shown below:

Title page,
Kindly insert as the first word in the title --NOVEL--.

Signed and Sealed this

Tenth Day of April, 2001

Attest:

NICHOLAS P. GODICI

*Attesting Officer*  *Acting Director of the United States Patent and Trademark Office*